(12) United States Patent
Kaiser et al.

(10) Patent No.: US 6,232,507 B1
(45) Date of Patent: May 15, 2001

(54) METHOD FOR NON-OXIDATIVE PRODUCTION OF FORMALDEHYDE FROM METHANOL

(75) Inventors: Thomas Kaiser, Kelkheim; Elke Schweers, Bad Soden; Christine Meister, Sulzbach, all of (DE)

(73) Assignee: Ticona GmbH (DE)

( * ) Notice: Subject to any disclaimer, the term of this patent is extended or adjusted under 35 U.S.C. 154(b) by 0 days.

(21) Appl. No.: 09/623,660
(22) PCT Filed: Mar. 8, 1999
(86) PCT No.: PCT/EP99/01471
  § 371 Date: Sep. 26, 2000
  § 102(e) Date: Sep. 26, 2000
(87) PCT Pub. No.: WO99/46228
  PCT Pub. Date: Sep. 16, 1999

(30) Foreign Application Priority Data

Mar. 10, 1998 (DE) .............................. 198 10 087

(51) Int. Cl.[7] .................................................. C07C 45/41
(52) U.S. Cl. .............................................................. 568/449
(58) Field of Search ............................................... 568/449

(56) References Cited

U.S. PATENT DOCUMENTS 6,124,480   9/2000   Hoffmockel et al. ................. 549/368

FOREIGN PATENT DOCUMENTS

| 1 645 451 | 10/1970 | (DE) . |
| 196 44 188 | 5/1998 | (DE) . |
| 198 14 281 | 12/1998 | (DE) . |
| 198 14 283 | 12/1998 | (DE) . |
| 198 14 285 | 12/1998 | (DE) . |
| 198 14 284 | 1/1999 | (DE) . |
| 0 294 684 | 12/1988 | (EP) . |
| 0 691 338 | 1/1996 | (EP) . |

*Primary Examiner*—Johann Richter
*Assistant Examiner*—Sikarl A. Witherspoon
(74) *Attorney, Agent, or Firm*—Connolly Bove Lodge & Hutz LLP

(57) ABSTRACT

Process for the nonoxidative preparation of formaldehyde from methanol The invention relates to a process for preparing formaldehyde from methanol by dehydrogenation in a reactor at temperatures in the range from 300 to 1000° C. in the presence of a catalyst which is introduced into the reactor with the aid of a carrier gas to give a product gas mixture, wherein the formaldehyde is separated from the product gas mixture and at least part of the remaining product gas mixture is recirculated to the reactor in a circulating gas stream and the carrier gas used is a carbon-free gas or gas mixture.

14 Claims, 2 Drawing Sheets

METHOD FOR NON-OXIDATIVE PRODUCTION OF FORMALDEHYDE FROM METHANOL

A number of processes for preparing formaldehyde from methanol are known (see, for example, Ullmann's Encyclopedia of Industrial Chemistry). Processes which are carried out industrially are predominantly the oxidation $$CH_3OH + \tfrac{1}{2}O_2 \rightarrow CH_2O + H_2O$$

over catalysts comprising iron oxide and molybdenum oxide at from 300° C. to 450° C. (Formox process) and the oxidative dehydrogenation (silver catalyst process) described by:

$$CH_3OH \rightarrow CH_2O + H_2$$

$$H_2 + \tfrac{1}{2}O_2 \rightarrow H_2O$$

at from 600° C. to 720° C. In both processes, the formaldehyde is initially obtained as an aqueous solution. Particularly when used for preparing formaldehyde polymers and oligomers, the formaldehyde obtained in this way has to be subjected to costly removal of water. A further disadvantage is the formation of corrosive formic acid which has an adverse effect on the polymerization as by-product.

The dehydrogenation of methanol enables these disadvantages to be avoided and, in contrast to the abovementioned processes, enables virtually water-free formaldehyde to be obtained directly:

$$CH_3OH \xrightarrow{cat.} CH_2O + H_2$$

In order to obtain an ecologically and economically interesting industrial process for the dehydrogenation of methanol, the following prerequisites have to be met: the strongly endothermic reaction has to be carried out at high temperatures in order to be able to achieve high conversions. 35 Competing secondary reactions have to be suppressed so as to achieve sufficient selectivity for formaldehyde (uncatalyzed, the selectivity to formaldehyde is less than 10% at conversions of over 90%). Residence times have to be short or the cooling of the reaction products has to be rapid in order to minimize the decomposition of the formaldehyde which is not thermodynamically stable under the reaction conditions:

$$CH_2O \rightarrow CO + H_2.$$

Various processes for carrying out this reaction have been proposed; thus, for example, DE-A-37 19 055 describes a process for preparing formaldehyde from methanol by dehydrogenation in the presence of a catalyst at elevated temperature. The reaction is carried out at a temperature of 300° C. to 800° C. in the presence of a catalyst comprising at least one sodium compound.

J. Sauer and G. Emig (Chem. Eng. Technol. 1995, 18, 284–291) were able to liberate a catalytically active species which they presumed to be sodium from a catalyst comprising $NaAlO_2$ and $LiAlO_2$ by means of a reducing gas mixture (87% of $N_2$+13% of $H_2$). This species is able to catalyze the dehydrogenation of methanol introduced downstream in the same reactor, i.e. not coming into contact with the catalyst bed, to produce formaldehyde. When nonreducing gases were used, only a slight catalytic activity was observed.

According to J. Sauer and G. Emig and also results from more recent studies (see, for example, M. Bender et al., paper at the 30th annual conference of German catalyst chemists, Mar. 21–23, 1997), sodium atoms and NaO molecules were identified as species emitted into the gas phase and their catalytic activity for the dehydrogenation of methanol in the gas phase was described. In the known processes, the starting material methanol is always diluted with nitrogen and/or nitrogen/hydrogen mixtures for the reaction.

Various publications, for example EP-A 0 130 068, EP-A 0 261 867 and DE-A 25 25 174 propose using the gas mixture formed in the reaction as fuel after separating off the formaldehyde.

Although the known processes already give good results, there is still plenty of room for improvements from engineering and economic points of view.

It is therefore an object of the invention to provide an improved and more economical process.

In the search for a solution to achieve this object, the following was found:

A great improvement in engineering and economic terms, particularly in respect of energy, can be achieved if the product gas mixture formed in addition to the formaldehyde is used for diluting the methanol starting material.

It is also advantageous to generate a catalytically active species from a primary catalyst in a carrier gas stream at a temperature which is different from the dehydrogenation temperature. The regions for generating the catalytically active species and for carrying out the reaction are advantageously physically separated from one another. This enables different temperatures and residence times to be set for the carrier gas streams passed through these units.

The circulating gas stream is obtained by, after separating off the formaldehyde, recirculating at least part of the by-products of the dehydrogenation, primarily $H_2$ and CO, to the reactor by means of a suitable apparatus.

Heating suitable primary catalysts in the primary catalyst decomposition zone and passing gas over them at temperatures which are different from the dehydrogenation temperature results in one or more catalytically active species which are able to catalyze the dehydrogenation of methanol being generated or carried out by the gas. Such a fluid catalyst is transported to the reaction zone via the feed lines. Setting the temperatures separately and matching them to the respective conditions for liberation/vaporization of catalyst or generation of a catalytically active species on the one hand and for the reaction on the other hand makes it possible, in particular, to lower the reaction temperature. This reduces the decomposition of the unstable formaldehyde as a result of secondary reactions and increases the yield.

Although the homogeneously catalyzed, nonoxidative dehydrogenation of methanol by means of sodium species in the gas phase and the introduction of the catalytically active species by thermal decomposition of a primary catalyst or vaporization of various substances has been described in the literature, attention has not previously been paid to possible losses of catalyst on the way to the reaction zone.

It has surprisingly been found that the catalyst utilization and formation of deposits in the region in which the active catalyst species is generated depends strongly on the carrier gases used.

When using $H_2$/CO mixtures or the circulating gas as carrier gas for the catalyst species, growing deposits comprising mainly carbon and additionally sodium, oxygen and hydrogen are formed in the feed line upstream of the actual reactor. This adversely affects the primary catalyst utilization, results in partial inactivation of the catalyst and limits the trouble-free operating time of the plant. This negative synergistic effect due to formation of a deposit and trapping of the catalyst impairs the economic operation of the plant.

Furthermore, it has surprisingly been found that it is possible to increase the primary catalyst utilization and to avoid the formation of deposits in the region of the catalyst feed line and the reactor inlet.

The invention accordingly provides a process for preparing formaldehyde from methanol by dehydrogenation in a reactor at temperatures in the range from 300 to 1000° C. in the presence of a catalyst which is introduced into the reactor with the aid of a carrier gas to give a product gas mixture, wherein the formaldehyde is separated from the product gas mixture and at least part of the remaining product gas mixture is recirculated to the reactor in a circulating gas stream and the carrier gas used is a carbon-free gas or gas mixture.

Particular embodiments are disclosed in the subclaims. One or more of these embodiments, either individually or in combination, can also achieve the object of the invention and the features of the embodiments can also be combined in any way.

The amount of catalyst-containing carrier gas stream as a proportion of the total gas stream is here from 1 to 50%, preferably from 5 to 40%.

The process of the invention makes it possible to obtain formaldehyde which is low in water in an ecologically and economically favorable way. The utilization of the hydrogen-rich by-products of the reaction, i.e. the product gas after separating off the formaldehyde, for diluting the methanol starting material for the dehydrogenation enables, on the one hand, particularly high yields to be achieved and, on the other hand, allows, owing to the good thermal conductivity, the equipment required for heating the starting materials, introducing the heat of reaction and for cooling the product to be minimized. The further possible utilization of parts off the by-products of the reaction, i.e. the product gas after separating off the formaldehyde, as fuel for generating the necessary reaction temperature for the dehydrogenation and also heat recovery from the waste gases enables the heat for this and further process steps to be recovered. It is then essentially only the desired product formaldehyde and the combustion products $CO_2$ and $H_2O$ which leave the process.

Furthermore, the process of the invention allows losses of catalyst on the way to the reaction zone and operating malfunctions of the plant caused by formation of deposits to be avoided. This also decreases the necessity for interruptions to production and for cleaning steps, which are undesirable from economic and ecological points of view.

Advantages of the lower reaction temperature lie in the reduced energy consumption and equipment requirement for heating/cooling before/after the reaction, the low decomposition rate of the formaldehyde which is thermally unstable under the reaction conditions and the low demands placed on the materials of construction.

For the purposes of the invention, dehydrogenation is a nonoxidative process described by the equation:

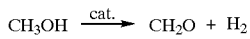

$$CH_3OH \xrightarrow{cat.} CH_2O + H_2$$

For the purposes of the invention, the circulating gas is the product gas mixture which remains after separating off the formaldehyde product and comprises hydrogen plus usually CO, $CH_4$ and $CO_2$ and also possibly $CH_2O$, MeOH, $H_2O$ and $HCOOCH_3$. It preferably consists essentially of $H_2$, CO, $CH_4$ and $CO_2$. The ratio of $H_2$/CO in the circulating gas is particularly preferably $\geq 3$.

Figure 1:
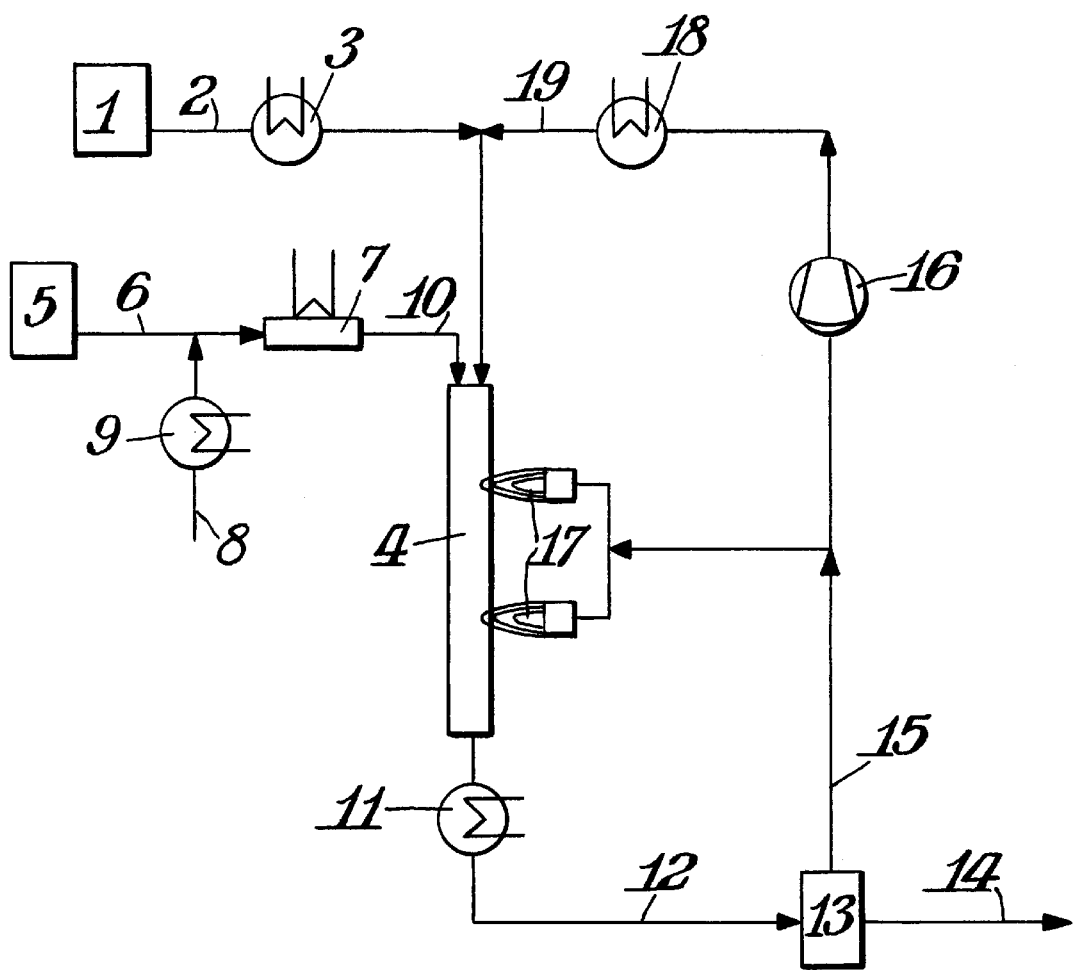
FIG. 1 gives an overview of a preferred variant of the process of the invention in the form of a schematic process flow diagram.

Methanol 2 from a reservoir 1 is preheated and vaporized in a heat exchanger 3 and, after dilution with circulating gas 19 preheated in a heat exchanger 18, is introduced into the reactor 4.

Primary catalyst 6 from a reservoir 5 is conveyed into the heated vessel 7 through which a carrier gas 8 which is heated by the heat exchanger 9 flows. This stream is likewise introduced into the reactor 4 via a line 10. After passing through the reactor 4, the gas stream is cooled in a heat exchanger 11 and the product gas mixture 12 is separated into formaldehyde 14 and by-products 15 (circulating gas) in the separation vessel 13. At least part of the by-products are recirculated to the reactor by means of a conveying device 16, for example a fan. Part of the by-products can, after discharge, be used directly as fuel in an apparatus for firing the reaction vessel 17.

The invention also provides an apparatus for carrying out the above-mentioned process, which comprises one or more heat exchangers for preheating the starting materials methanol and circulating gas, a unit for liberating the catalyst into a substream of carrier gas, a reactor for carrying out the dehydrogenation, a heat exchanger for cooling the product gas mixture, a separation vessel for separating off the formaldehyde and also means, in particular a fan, of recirculating at least part of the by-products of the reaction to the reactor.

In a preferred embodiment of the apparatus of the invention, this further comprises means of discharging a further part of the by-products of the dehydrogenation and conveying this part to an apparatus where it serves as fuel for heating the reactor.

The reaction can be carried out using commercial methanol which is preferably low in water and contains no materials which poison the catalyst.

To carry out the dehydrogenation, the fluid, preferably gaseous, methanol is diluted with gaseous by-products of the dehydrogenation.

The mol fraction of methanol is generally from 5 to 90%, preferably from 10 to 60%, particularly preferably from 10 to 50%. The proportion of methanol determines the amount of circulating gas required.

Primary catalysts used in the process of the invention are preferably sodium-containing compounds, particularly preferably metallic sodium and sodium alkoxides of a lower ($C_1$–$C_6$) alcohol.

When used as catalysts in a plant corresponding to FIG. 1, the above-mentioned compounds give formaldehyde yields of over 70% and low water concentrations of less than 5 mol % of $H_2O$ per mol of formaldehyde.

The further introduction of the primary catalyst as solid, e.g. in powder form, as granules or compacted, is carried out by means of a solids metering device, e.g. with reciprocating or rotary piston, cellular wheel feeder, screw or vibratory chute.

If the primary catalyst is added in the form of a solution, particularly suitable solvents are those having a chemical composition consisting only of elements which are already present in the process (C, H, O) and thus do not interfere. Particular preference is given to using MeOH as solvent. The addition is carried out, for example, by means of a nozzle which can be cooled in order to avoid vaporization of the solvent and crystallization or deposition of the solid primary catalyst in the nozzle.

The addition of the primary catalyst as a melt is possible, for example, via a nozzle. The melt can then be vaporized or decomposed directly in the gas stream.

This can be achieved, for example, by applying the catalyst material according to the above-described processes to a suitable surface through or over which the gas flows. The surface can be the surface of a support material which is present as a fixed bed of particulate material. Examples of suitable materials are SiC, $SiO_2$, $Al_2O_3$, etc., in a suitable geometric form, e.g. as granules, pellets or spheres. The material is preferably arranged vertically in the fixed bed, preferably with metering-in from above. The substance introduced deposits on the support material and the catalytically active substance goes into the gas phase during the process.

Another possibility is arranging the primary catalyst in a fluidized bed through which the carrier gas stream is passed. Here, the fluidized material consists at least partly of the supported or unsupported primary catalyst.

The loss of active substance can be made up by introduction of further fresh primary catalyst and exhausted material can likewise be taken off. In the continuous case, this can be achieved, for example, by means of a circulating fluidized bed.

The further introduction of a primary catalyst can also be carried out by alternate generation of secondary catalyst in various vessels in which the primary catalyst can be present as, for example, a fixed bed or fluidized bed, in each case supported or unsupported.

The advantage of using a plurality of units for the discontinuous introduction of further catalyst is that it is also possible to use those primary catalysts for which, e.g. owing to material properties such as melting point, viscosity or decomposition temperature, continuous feeding would be possible only with great difficulty, if at all.

Suitable reactors are well known to those skilled in the art. It is basically possible to use reactor types and constructions as are known from the literature for dehydrogenation reactions. Such apparatuses are described, for example, in Winnacker/Küchler, Chemische Technologie, 4th edition, chapter "Technik der Pyrolyse", Hanser Verlag, Munich 1981–86.

Examples of suitable reactors are tube reactors and suitable reactor materials are, for example, ceramic materials such as alumina and also iron- and nickel-based alloys which are resistant to carbonization, heat and scale formation, e.g. Inconel 600® or Hasteloy®.

The heat to be supplied to the process is preferably obtained by combustion of by-products of the dehydrogenation, primarily $H_2$ and CO, which have been discharged from the circular process.

If the reactor is heated by means of a combustion reaction, a suitable reactor is, for example, an externally fired tube reactor.

It is likewise possible to heat the reactor by means of microwaves.

The formaldehyde can be separated from the reaction mixture by methods which are known per se and with which those skilled in the art are familiar, for example by condensation, polymerization or physical or chemical absorption or adsorption.

An industrially proven method is the formation of hemiacetals from formaldehyde and an alcohol. The hemiacetals are subsequently dissociated thermally, giving very pure formaldehyde vapor. The alcohol used is usually cyclohexanol since its boiling point is sufficiently far above the decomposition of the hemiacetal. The hemiacetals are usually dissociated in falling-film or thin-film evaporators at temperatures of from 100 to 160° C. (see, for example, U.S. Pat. No. 2,848,500 of Aug. 19, 1958 "Preparation of Purified Formaldehyde" and U.S. Pat. No. 2,943,701 of Jul. 5, 1960 "Process for purification of gaseous formaldehyde" or JP-A 62/289 540). The formaldehyde vapors liberated still contain small amounts of impurities which are usually removed by a countercurrent scrub with alcohol, e.g. cyclohexanol hemiformal, by condensation or by controlled prepolymerization.

A further method of separating formaldehyde from the reaction mixture is the formation of trioxane in a catalytic gas-phase process (see, for example, Appl. Catalysis A 1997, 150, 143–151 and EP-A 0 691 338). Trioxane can then, for example, be condensed out.

Possible uses of the by-products of the reaction, in particular hydrogen, are, for example, the synthesis of methanol or the isolation of pure hydrogen which can be separated off, for example, by means of membranes.

Hydrogen obtained in this way is suitable, for example, for the synthesis of ammonia, in refinery processes for producing gasoline and petrochemical cracking products, for the synthesis of methanol, for solidification of fats and other hydrogenations, as reducing agent for producing W, Mo, Co and other metals, as reducing protective gas in metallurgical processes, for autogenous welding and cutting, as fuel gas in admixture with other gases (town gas, water gas), or in liquefied form as fuel in aerospace applications.

The formaldehyde prepared by the process of the invention is suitable for all known applications, for example corrosion protection, mirror production, electrochemical coatings, for preparing methanolic formaldehyde solutions and methylal, as disinfectant and preservative, likewise as intermediate for producing plastics, for example polyacetals (polyoxymethylenes), phenolic resins, melamines, amino plastics, polyurethanes and casein plastics, 1,4-butanols, trimethylolpropane, neopentyl glycol, pentaerythritol and trioxane, for producing dyes such as fuchsin, acridine, for producing fertilizers and for the treatment of seed.

Since formaldehyde prepared by the process of the invention usually has a low water content, formaldehyde produced in this way is particularly suitable for polymerization to form polyoxymethylene and trioxane, since water-free formaldehyde has to be used here. The invention also provides plastics such as polyoxymethylene and polyacetals, trioxane, dyes, fertilizers and seed produced in such a way.

The invention is illustrated by the examples without being restricted thereby.

EXAMPLES

The yield is calculated as follows:

$$\text{yield (in \%)} = \frac{\text{formaldehyde formed (mol)}}{\text{methanol fed in (mol)}} \cdot 100\%$$

Figure 2:
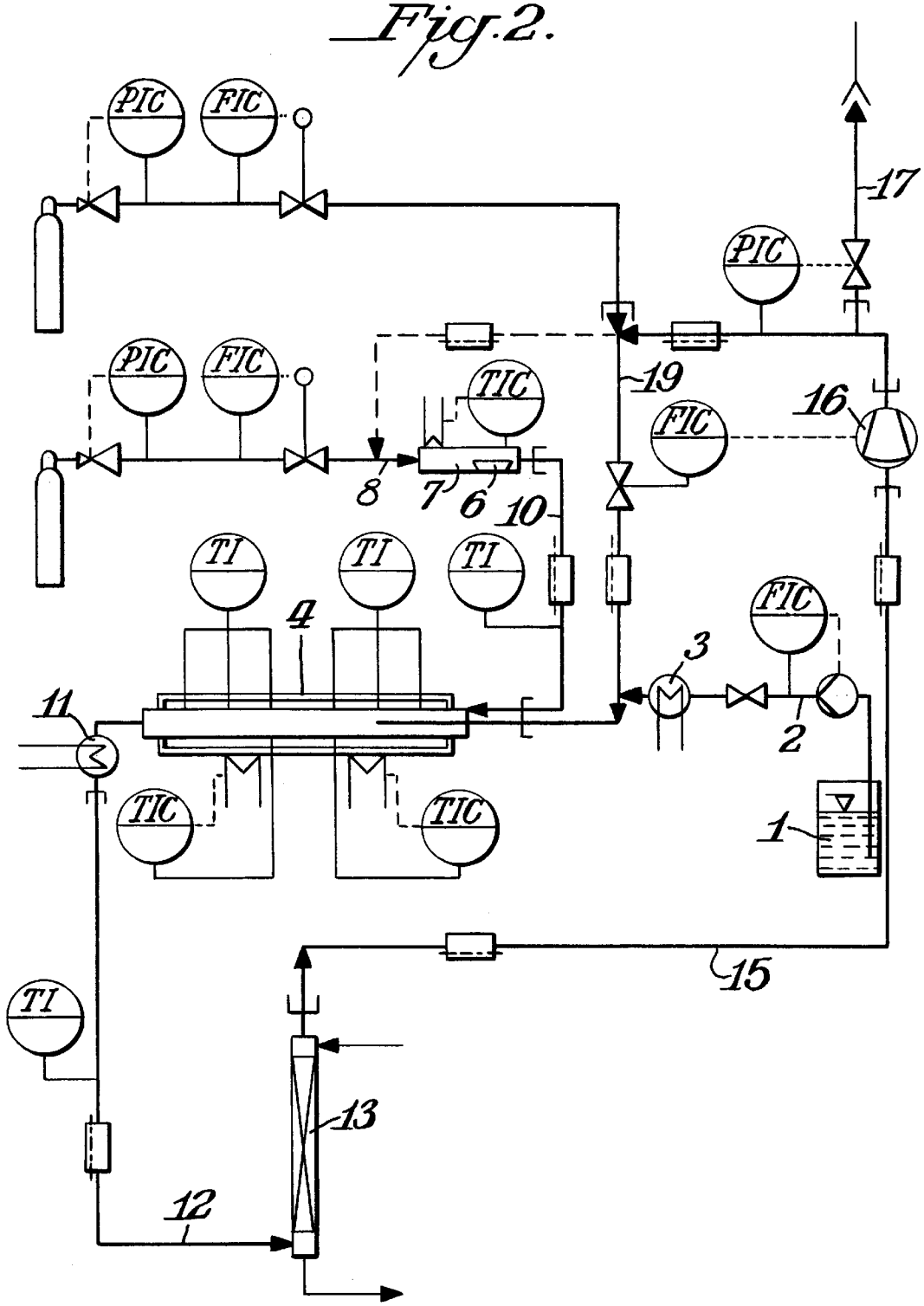

A. Electrically Heated Tube Reactor:

The dehydrogenation of methanol is carried out in a tube reactor 4 which is indirectly heated by an electric tube furnace (configuration of the test apparatus as shown in the flow diagram in FIG. 2). The catalyst-containing stream is generated by passing a carrier gas stream 8 (nitrogen, hydrogen or argon and/or $H_2$/CO or circulating gas) over a boat containing primary catalyst 6 (metallic sodium or sodium methoxide) which is located in a heated metal tube 7. The methoxide is decomposed or the sodium is vaporized. The stream is passed into the reaction space via a heated transfer line 10 whose temperature is higher than that in the metal tube used for catalyst decomposition 7.

Methanol 2 is conveyed by means of a pump and preheated or vaporized by means of a heat exchanger 3, introduced into the circulating gas stream 19, heated further to a temperature close to the reaction temperature and likewise introduced into the reaction space 4. The reaction space is formed by a tube having a length of 300–450 mm and an internal diameter of 11 mm. The reactor temperature is 600–850° C. The total flow is 100–500 l/h. The methanol feed rate is such that a methanol concentration of about 10–20 mol % is established.

After leaving the reactor, the product gases 12 are rapidly cooled to a temperature of less than 200° C. in a cooler 11 and analyzed by means of a gas chromatograph. The reaction products are scrubbed with alcohol (e.g. cyclohexanol at 20–80° C.) in a column 13 in order to separate out the formaldehyde. The gaseous by-products are recirculated using a fan 16 and an excess 17 is discharged.

To assess the catalyst utilization and the formation of deposits, the lines carrying the catalyst were cleaned mechanically and purged after each test, the amount of deposits was determined and the deposits were, if appropriate, analyzed.

Test Conditions:

running-up of the plant using $H_2/CO$ (about 15% of CO) before switching over to circulating gas circulating gas stream comprising a product gas mixture after scrub or $H_2/CO$ (about 15% of CO)

200–350 l/h of total carrier gas stream through the reactor,
20–100 l/h of carrier gas stream through catalyst liberation
42–56 g/h of methanol, Temperatures Set:

furnace temperature in catalyst liberation 300–700° C.,
transfer line 500–700° C.,
furnace temperature in reactor 750–900° C.

TABLE 1

Formaldehyde yield and formation of sodium-containing deposits in the dehydrogenation of methanol

| Example Comparative Example | Catalyst | Carrier gas over catalyst | Yield of formaldehyde | Deposits in catalyst transfer line |
|---|---|---|---|---|
| Ex. 1 | Na | $N_2$ | 73 | None |
| Ex. 2 | Na | $N_2$ | 70 | None |
| Ex. 3 | Na methoxide | $N_2$ | 69 | None |
| Ex. 4 | Na | $H_2$ | 65 | None |
| Ex. 5 | Na | Ar | 68 | None |
| Ex. 6 | Na methoxide | Ar | 65 | None |
| Comp. Ex. 1 | Na | $H_2/CO$ | 68 | Line blocked after 3 h, deposit comprising C, Na, H and O |
| Comp. Ex. 2 | Na methoxide | $H_2/CO$ | 65 | Line blocked after 5 h, deposit comprising C, Na, H and O |

What is claimed is:

1. A process for preparing formaldehyde from methanol by dehydrogenation in a reactor at temperatures in the range from 300 to 1000° C. in the presence of a catalyst which is introduced into the reactor with the aid of a carrier gas to give a product gas mixture, wherein the formaldehyde is separated from the product gas mixture and at least part of the remaining product gas mixture is recirculated to the reactor in a circulating gas stream and the carrier gas used is a carbon-free gas or gas mixture.

2. The process as claimed in claim 1, wherein the carbon-free gas is nitrogen or hydrogen or a noble gas or a mixture of these gases.

3. The process as claimed in claim 1, wherein the amount of carbon-free carrier gas via the catalyst introduction makes up from 1 to 60% of the total gas stream.

4. The process as claimed in claim 1, wherein the catalyst used is sodium.

5. The process as claimed in claim 1, wherein the catalyst used is a sodium alkoxide of a lower ($C_1$–$C_6$) alcohol.

6. The process as claimed in claim 1, wherein the reactor is an externally fired tube reactor.

7. The process as claimed in claim 1, wherein part of the by-products of the dehydrogenation is used for energy recovery or as fuel for heating the reactor.

8. The process as claimed in claim 1, wherein the hydrogen formed as by-product is separated off and used elsewhere.

9. A process for preparing trioxane, which comprises preparing formaldehyde from methanol by dehydrogenation in a reactor at temperatures in the range from 300 to 1000° C. in the presence of a catalyst which is introduced into the reactor with the aid of a carrier gas to give a product gas mixture from which the formaldehyde is separated off and at least part of the remaining product gas mixture is recirculated to the reactor in a circulating gas stream, wherein the carrier gas used is a carbon-free gas or gas mixture, and trimerizing the formaldehyde obtained in this way to give trioxane.

10. A process for preparing polyoxymethylene, which comprises preparing formaldehyde from methanol by dehydrogenation in a reactor at temperatures in the range from 300 to 1000° C. in the presence of a catalyst which is introduced into the reactor with the aid of a carrier gas to give a product gas mixture from which the formaldehyde is separated off and at least part of the remaining product gas mixture is recirculated to the reactor in a circulating gas stream, wherein the carrier gas used is a carbon-free gas or gas mixture, and optionally, purifying the formaldehyde, and polymerizing the formaldehyde.

11. The process as claimed in claim 2, wherein the amount of carbon-free carrier gas via the catalyst introduction makes up 1 to 60% of the total gas stream.

12. The process as claimed in claim 11, wherein the catalyst used in sodium.

13. The process as claimed in claim 11, wherein the catalyst used is a sodium alkoxide of a lower ($C_1$–$C_6$) alcohol.

14. The process as claimed in claim 13, wherein the reactor is an externally fired tube reactor.

* * * * *